United States Patent [19]
Riechers et al.

[11] Patent Number: 6,160,178
[45] Date of Patent: Dec. 12, 2000

[54] RACEMIZATION OF OPTICALLY ACTIVE AMINES

[75] Inventors: Hartmut Riechers, Neustadt; Joachim Simon, Mannheim; Arthur Höhn, Kirchheim; Andreas Kramer, Freinsheim; Frank Funke; Wolfgang Siegel, both of Limburgerhof; Christoph Nübling, Hassloch, all of Germany

[73] Assignee: BASF Aktiengesellschaft, Ludwigshafen, Germany

[21] Appl. No.: 09/303,599

[22] Filed: May 3, 1999

[30] Foreign Application Priority Data

Nov. 13, 1998 [DE] Germany .............. 198 52 282
Dec. 23, 1998 [DE] Germany .............. 198 59 775

[51] Int. Cl.$^7$ .................................................. C07C 209/00
[52] U.S. Cl. ................................................ 564/302
[58] Field of Search ............................................ 564/302

[56] References Cited

U.S. PATENT DOCUMENTS 4,096,186  6/1978  Ichikawa et al. ............... 260/584
4,990,666  2/1991  Harsy ............................ 564/302

FOREIGN PATENT DOCUMENTS 2851039     6/1980   Germany .
2903589     8/1980   Germany .
199 05 837  2/1999   Germany .
199 05 838  2/1999   Germany .
6135906    10/1992   Japan .

OTHER PUBLICATIONS

Database WPI, Section Ch, Week 7908, Derwent Publications Ltd., London, GB:Class B05, AN 79–14874B, XP002112502 (English abstract of JP 54 005957, Jan. 17, 1979).

Database WPI, Section Ch, Week 9424, Derwent Publications Ltd., London, GB: Class B05, AN 94–197043, XP002112503 (English abstract of JP 06 135906, May 17, 1994).

Chem. Abst., vol. 110, 192247v, Jun., 1989.

Primary Examiner—Samuel Barts
Attorney, Agent, or Firm—Keil & Weinkauf

[57] ABSTRACT

Optically active amines are racemized by reaction of the optically active amine in the gas phase at elevated temperature in the presence of hydrogen and a hydrogenation or dehydrogenation catalyst.

12 Claims, No Drawings

RACEMIZATION OF OPTICALLY ACTIVE AMINES

The present invention relates to a process for the racemization of optically active amines of the formula I

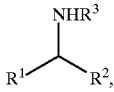

(I)

where $R^1$ and $R^2$ are different and $R^1$, $R^2$, $R^3$ are alkyl, cycloalkyl, arylalkyl, aryl, heteroaryl and heterocyclic radicals and $R^3$ can also be hydrogen (H), where the radicals can bear substituents selected from the group consisting of alkyl, cycloalkyl, alkoxy, aryloxy, amino, alkylamino and dialkylamino, by reaction of the optically active amine in the presence of hydrogen and a hydrogenation or dehydrogenation catalyst at elevated temperature.

Optically active amines of the formula I are, for example, valuable pharmaceuticals and intermediates for preparing active compounds (cf., for example: DE-A-29 03 589, page 2, lines 17 to 26). Since frequently only one of the two enantiomers (on the basis of the asymmetric carbon atom shown in I) is active or is more active than the other enantiomer, processes are required for the racemization of the less active enantiomer which is obtained, for example, in the resolution of the corresponding racemic amine by known methods, so that the more active enantiomer can again be isolated from the racemized amine by known methods (e.g. resolutuion).

IN-A-162 213 (Chem. Abstracts 110: 192247v) discloses a process for preparing racemic 2-aminobutanol by treating 1-2-aminobutanol with ammonia in the presence of $Rh/Al_2O_3$.

U.S. Pat. No. 4,096,186 describes a process for the racemization of optically active aminoalcohols in which the aminoalcohol, preferably in the liquid phase, is brought into contact with ammonia and hydrogen in the presence of a hydrogenation catalyst which preferably comprises cobalt. In the reaction of optically active 2-amino-1-butanol, the degree of racemization achieved is only 63% at a racemate yield of at most 97.6%. On the other hand, at a degree of racemization of 99%, the racemate yield achieved is only 75.1%.

U.S. Pat. 4,990,666 discloses a process for the racemization of optically active aminoalcohols in which the aminoalcohol is brought into contact with Raney cobalt in the presence of hydrogen. This patent teaches that high temperatures, e.g. greater than 160° C., reduce the racemate yield. Furthermore, according to these teachings, the racemization is carried out in the liquid phase in the presence of an inert solvent.

JP-A-06 135 906 (Derwent Abstract No. 94-197043/24; Chem. Abstracts 121: 179093z) describes a process for the racemization of optically active vicinal primary diamines in the presence of hydrogen and a hydrogenation catalyst such as Raney nickel or Raney cobalt.

DE-A-28 51 039 describes a process for preparing racemic mixtures of optically active 1-arylamines in which the optically active 1-arylamines are treated with hydrogen in a liquid phase in the presence of a hydrogenation catalyst, in particular Raney cobalt.

DE-A-29 03 589 describes a process for preparing racemic mixtures of optically active amines by treating the optically active amines with hydrogen in the presence of a hydrogenation catalyst at elevated temperature. This document teaches carrying out the racemization of the optically active amine, depending on the nature of the amine, in solvents or in bulk, i.e. in liquid or solid form. The reaction of optically active 2-amino-1-phenyl-propane in the liquid phase for a reaction time of 12 hours over a Raney cobalt catalyst leads, at a degree of racemization of at most 98%, to a racemate yield of only 91.1%.

It is an object of the present invention to discover an improved, economical process for the racemization of optically active amines in which the process product is obtained with a high degree of racemization and at the same time in a high racemization yield and a high space-time yield.

We have found that this object is achieved by a process for the racemization of optically active amines of the formula I

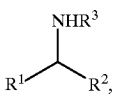

(I)

where $R^1$ and $R^2$ are different and $R^1$, $R^2$, $R^3$ are alkyl, cycloalkyl, arylalkyl, aryl, heteroaryl and heterocyclic radicals and $R^3$ can also be hydrogen (H), where the radicals can bear substituents selected from the group consisting of alkyl, cycloalkyl, alkoxy, aryloxy, amino, alkylamino and dialkylamino, by reaction of the optically active amine in the presence of hydrogen and a hydrogenation or dehydrogenation catalyst at elevated temperature, wherein the reaction is carried out in the gas phase.

The gas-phase process of the present invention can be carried out batchwise or preferably continuously as follows, with the catalyst preferably being arranged as a fixed bed in the reactor.

The process of the present invention can be carried out in the absence or preferably in the presence of the amine of the formula $R^3NH_2$, where the radical $R^3$ corresponds to the radical $R^3$ of the optically active amine I (e.g. the presence of the amine ammonia in the case of racemization of optically active amines I in which $R^3$=H).

If the reaction is carried out in the presence of the amine $R^3NH_2$, the molar ratio of $R^3NH_2$ to amine I is generally from 1:1 to 50:1, preferably from 1.5:1 to 30:1, particularly preferably from 2:1 to 20:1, very particularly preferably from 2:1 to 10:1. The $R^3NH_2$ excess based on the amine I can also be greater than 50:1.

The hydrogen is generally introduced into the reaction in an amount of from 5 to 400 l, preferably in an amount of from 50 to 200 l, per mol of amine component I, with the liter values in each case being at STP.

The optically active amine I is passed continuously in gas form at pressures of from 0.1 to 10 MPa, preferably from 0.1 to 5 MPa, particularly preferably from 0.1 to 3 MPa, over the catalyst in a tube reactor in a gas stream comprising hydrogen and advantageously the amine $R^3NH_2$ or ammonia, preferably comprising hydrogen with or without the amine $R^3NH_2$ or ammonia, and having a flow which is sufficiently high for vaporization.

It is possible for the feed stream to flow into the fixed bed of catalyst from above or from below. The gas stream required is preferably obtained by means of a circulating gas procedure using, for example, a circulated gas flow of from about 5 to 10 $m^3$/h (volume at STP) and a gas outflow of from about 250 to 350 l/h at a catalyst bed volume of 1 l. The space velocity over the catalyst is generally in the range from 0.1 to 2 kg, preferably from 0.1 to 1 kg, particularly preferably from 0.2 to 0.6 kg, of amine I per liter of catalyst (bed volume) an hour.

The temperatures selected for the racemization are in the range from 100 to 300° C., preferably from 150 to 270° C., particularly preferably from 160 to 250° C., very particularly preferably from 170 to 240° C., in particular from 180 to 230° C.

It is possible to employ higher temperatures, higher total pressures and higher space velocities over the catalyst than those given above. The pressure in the reaction vessel, which is essentially the sum of the partial pressures of the amine component I, any amine $R^3NH_2$ present and the racemized amine formed at the temperature employed, is conveniently increased to the desired reaction pressure by injection of hydrogen.

After the reaction output has been appropriately depressurized, the hydrogen and any amine of the formula $R^3NH_2$ which has been used are removed and can be recirculated, and the cooled crude reaction product obtained, which contains essentially the racemic amine I, is purified by fractional rectification at atmospheric pressure or under reduced pressure.

Particularly suitable hydrogenation catalysts and dehydrogenation catalysts are catalysts which comprise, as catalytically active constituents, elements selected from the group consisting of copper, silver, gold, iron, cobalt, nickel, rhenium, ruthenium, rhodium, palladium, osmium, iridium, platinum, chromium, molybdenum and tungsten, in each case in metallic form (oxidation state 0) or in the form of compounds, e.g. oxides, which are reduced to the corresponding metal under the process conditions.

Preference is given to catalysts which comprise, as catalytically active constituents, elements selected from the group consisting of copper, silver, cobalt, nickel, ruthenium, rhodium, palladium, platinum, chromium and molybdenum, in particular selected from the group consisting of copper, silver, nickel, ruthenium, rhodium, palladium, chromium and molybdenum, in each case in metallic form (oxidation state 0) or in the form of compounds, e.g. oxides, which are reduced to the corresponding metal under the process conditions.

Preference is given to catalysts which comprise the catalytically active constituents copper, silver, gold, iron, cobalt, nickel, rhenium, ruthenium, rhodium, palladium, osmium, iridium, platinum, chromium, molybdenum and/or tungsten and a support material selected from the group consisting of aluminum oxide, zirconium dioxide, titanium dioxide, silicon dioxide and/or carbon.

In these preferred catalysts, the support materials aluminum oxide ($Al_2O_3$), zirconium dioxide ($ZrO_2$), titanium dioxide ($TiO_2$), silicon dioxide ($SiO_2$) and/or carbon are generally present in the catalytically active composition in total amounts of from 20 to 99.9% by weight, preferably from 30 to 99.9% by weight.

Examples of suitable catalysts are thin-layer catalysts in which the catalytically active components are applied to structured supports or monoliths, as are defined, for example, in the German application No. 198 27 385.1 of Jun. 27, 1998, page 1, lines 14 to 30, and in DE-A-35 13 726. The catalytically active components are applied to the structured support or monolith used, e.g. a metal wire mesh or an $SiO_2$-, $TiO_2$-, $ZrO_2$- or $Al_2O_3$ honeycomb body, by known methods, for example by vapor deposition of the catalytically active metal, e.g. noble metal, under reduced pressure as described in DE-A-35 13 726 or by an impregnation process as described in DE-A-41 35 055, DE-A-39 15 685 or U.S. Pat. No. 4,746,537.

Examples of thin-layer catalysts which can be used in the process of the present invention are the catalysts disclosed in EP-A-646 562 in Examples 1 and 2 which comprise the material No. 1.4767 (Kanthal) and vapor-deposited Pd, the catalyst disclosed in Example 3 which comprises the material No. 1.4401 and vapor-deposited Pd and the catalyst disclosed in Example 4 which comprises the material No. 1.4301 and vapor-deposited Pd. (Material numbers as given in "Stahleisenliste", Verlag Stahleisen mbH 1990, 8th edition, p. 87ff).

Further hydrogenation and dehydrogenation catalysts which are suitable for use in the process of the present invention are shell catalysts in which the catalytically active composition has been applied in the form of a shell on a core of support material which is generally inert under the reaction conditions, for example quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures thereof.

Such shell catalysts are usually prepared using impregnation processes as are described in J.-F. Le Page et al., Applied Heterogeneous Catalysis, Edition Technip Paris, 1987, ISBN 2-7108-0531-6, pages 106 to 123. These impregnation processes comprise (a) impregnation of the support material with an excess of solution (immersion) or (b) spray impregnation of the support material in an impregnation drum, followed in each case by drying and calcination.

Another possible way of preparing such shell catalysts is described, for example, in DE-A-16 42 938 and DE-A-17 69 998. In this method, an aqueous and/or organic solvent-containing solution or suspension of the constituents of the catalytically active composition and/or their precursor compounds, hereinafter referred to as the "slurry", is sprayed onto the support material in a heated coating drum at elevated temperature until the desired proportion by weight of catalytically active composition in the overall catalyst has been reached. According to DE-A-21 06 796, coating can also be carried out in fluidized-bed coaters, as are described, for example, in DE-A-12 80 756. The slurry can, if desired, include organic binders, preferably gcopolymers such as vinyl acetate-vinyl laurate or vinyl acetate-ethylene, as taught by EP-A-744 214.

Examples of shell catalysts which can be used in the process of the present invention are the catalysts disclosed in DE-A-20 59 978, Example 1 (cat. A), which are prepared by impregnation of alumina agglomerates with an aqueous noble metal salt solution, e.g. Pd salt solution, and subsequent drying and calcination, and the catalysts disclosed in the abovementioned article by J.-F. Le Page et al. (Applied Heterogeneous Catalysis), e.g. on page 110, which are prepared by impregnation and comprise $Al_2O_3$ and Ni and/or Co.

In general, the catalysts in the process of the present invention can also be used in the form of catalysts which have been obtained by impregnation, precipitation or peptization processes and which consist entirely of catalytically active composition and, if desired, a shaping aid (e.g. graphite or stearic acid) if the catalyst is used as a shaped body, i.e. no further catalytically inactive accompanying materials.

As supports, preference is given to using oxidic, carbidic or nitridic materials, particularly preferably materials of an oxidic nature.

In this context, materials used as catalyst supports, for example titanium dioxide ($TiO_2$; anatase, rutile), aluminum oxide ($Al_2O_3$; preferably α-, β-, γ- or θ-$Al_2O_3$; D10-10 from BASF; $Al_2O_3$ having a large surface area prepared by bringing at least one precursor of aluminum oxide into contact with at least one structure former in a liquid medium, e.g. as described in the German application No. 197 30 126.6 of Jul. 14, 1997, which is hereby expressly incorporated by reference), zirconium dioxide ($ZrO_2$; preferably in the monoclinic or tetragonal form), silicon dioxide ($SiO_2$; e.g. $SiO_2$ obtained by precipitation from water glass or by the sol-gel method or mesoporous $SiO_2$, e.g. mesoporous $SiO_2$ having a specific surface area of the mesopores of at least 500 $m^2/g$ and a pore volume of the mesopores of at least 1.0 ml/g as described in DE-A-196 39 016, or silica gel (e.g. as described in Ullmann, Enzykl. Techn. Chem., 4th edition, Volume 21, pp. 457–63, 1982) or in the form of silicates such as aluminosilicates (e.g. as described in Nature, Volume 359, pp. 710–12, 1992, or alkali metal or alkaline earth metal aluminosilicates (zeolites), e.g. of the formula $M_{2/z}O \cdot Al_2O_3 \cdot xSiO_2 \cdot yH_2O$, where M is a monovalent or polyvalent metal, H, [$NH_4$], z is the valence, x=1.8 to about 12 and y=0 to about 8), magnesium silicates (e.g. steatite), zirconium silicates, cerium silicates or calcium silicates) or $SiO_2$ having a large surface area prepared by bringing at least one precursor of silicon dioxide into contact with at least one structure former in a liquid medium, e.g. as described in the German application No. 197 32 865.2 of Jul. 30, 1997), clays which consist predominantly of phyllosilicates and/or chain silicates (e.g. bentonite or montmorillonite), pumice, silicon carbide, magnesium oxide (MgO), zinc oxide (ZnO), tin dioxide ($SnO_2$), cerium dioxide ($CeO_2$), and/or carbon (e.g. activated carbon or graphite in extruded or pelletized form), or mixtures thereof, are counted as being part of the catalytically active composition.

The catalytically active constituents copper, silver, gold, iron, cobalt, nickel, rhenium, ruthenium, rhodium, palladium, osmium, iridium, platinum, chromium, molybdenum and/or tungsten are generally present in the catalytically active composition of the catalyst in total amounts of from 0.1 to 80% by weight, preferably from 0.1 to 70% by weight and particularly preferably from 0.1 to 60% by weight, calculated as metal in the oxidation state 0.

The catalysts are used by introducing the catalytically active composition ground to powder form into the reactor or preferably placing the catalytically active composition, after milling, mixing with shaping aids, shaping and heat treatment, as shaped catalyst bodies, for example as pellets, spheres, rings or extrudates, in the reactor.

Various methods of preparing these catalysts are possible.

They are obtainable, for example, by peptization of pulverulent mixtures of the hydroxides, carbonates, oxides and/or other salts of the catalyst components with water and subsequent extrusion and heat treatment of the composition obtained in this way.

The catalysts used in the process of the present invention can also be prepared by impregnation of the catalyst support materials (see above) or mixtures of two or more of these catalyst support materials which are, for example, in the form of powder or shaped bodies such as extrudates, pellets, spheres or rings.

The shaped bodies of the abovementioned catalyst support materials can be produced by the customary methods.

The impregnation of the catalyst support material is likewise carried out by the customary methods, as described, for example, in EP-A-599 180, EP-A-673 918 or A. B. Stiles, Catalyst Manufacture -Laboratory and Commercial Preparations, Marcel Dekker, New York (1983), by application of an appropriate metal salt solution in one or more impregnation steps, using, for example, appropriate nitrates, acetates or chlorides as metal salts. After the impregnation, the composition is dried and, if desired, calcined.

The impregnation can be carried out by the incipient wetness method in which the catalyst support material is, depending on its water absorption capacity, moistened to at most saturation with the impregnation solution. However, the impregnation can also be carried out in supernatant solution.

In multistage impregnation processes, it is advantageous to dry and possibly calcine the support material between individual impregnation steps. It is particularly advantageous to employ multistage impregnation when the catalyst support material is to be loaded with a relatively large amount of metal.

To apply a plurality of metal components to the catalyst support material, the impregnation can be carried out simultaneously with all metal salts or successively in any order of the individual metal salts.

It is also possible to employ precipitation methods to prepare the catalysts used in the process of the present invention. Thus, for example, they can be obtained by coprecipitation of the metal components from an aqueous salt solution containing these elements by means of mineral bases in the presence of a slurry or suspension of fine powders of the sparingly soluble catalyst support material and subsequent washing, drying and calcination of the precipitate obtained. Sparingly soluble catalyst support materials which can be used are, for example, aluminum oxide, titanium dioxide, silicon dioxide, zirconium dioxide and/or hydrated zirconium oxide.

The catalysts used in the process of the present invention can be prepared by coprecipitation of all their components. For this purpose, an aqueous salt solution containing the catalyst components is conveniently admixed hot and while stirring with an aqueous mineral base, in particular an alkali metal base, for example sodium carbonate, sodium hydroxide, potassium carbonate or potassium hydroxide, until precipitation is complete. The type of salts used is generally not critical: since the water-solubility of the salts is of prime importance in this procedure, a criterion is that they have the good water-solubility necessary to prepare these comparatively highly concentrated salt solutions. It is considered self evident that, when selecting the salts of the individual components, only salts containing anions which do not lead to problems, whether by causing undesirable precipitation or by hindering or preventing precipitation by complex formation, will be selected.

The precipitates obtained in these precipitation reactions are generally chemically nonuniform and comprise, inter alia, mixtures of the oxides, hydrated oxides, hydroxides, carbonates and insoluble and basic salts of the metals used. To improve the filterability of the precipitates, it may prove to be useful to age them, i.e. to leave them to stand for some time after the precipitation, possibly at elevated temperature or while passing air through the suspension.

The precipitates obtained by these precipitation methods are further processed by customary methods to give the catalyst. After washing, they are generally dried at from 80 to 200° C., preferably from 100 to 150° C., and then calcined. The calcination is generally carried out at from 300 to 800° C., preferably from 400 to 600° C., in particular from 450 to 550° C.

After calcination, the catalyst is advantageously conditioned, whether by adjusting it to a particular particle size by milling or by mixing it after milling with shaping aids such as graphite or stearic acid, pressing it into compacts, e.g. pellets, by means of a press and heat treating it. The heat treatment temperatures generally correspond to the calcination temperatures.

In the catalysts prepared in this way, the catalytically active metals are present in the form of a mixture of their oxygen-containing compounds, i.e. particularly as oxides and mixed oxides.

The catalysts prepared in this way are usually prereduced before they are used for the racemization of the optically active amines I. However, they can also be used without prereduction, in which case they are then reduced under the conditions of the racemization by the hydrogen present in the reactor.

For the prereduction, the catalysts are generally first exposed to a nitrogen/hydrogen atmosphere at from 150 to 200° C. for a period of from 12 to 20 hours and subsequently treated in a hydrogen atmosphere at from 200 to 400° C. for up to about 24 hours. In this prereduction, part of the oxygen-containing metal compounds present in the catalysts are reduced to the corresponding metals, so that these together with the various oxygen compounds are present in the active form of the catalyst.

The following concentration figures (in % by weight) of the components of the catalyst are in each case based, unless otherwise indicated, on the mass of the catalytically active composition of the finished catalyst after its last heat treatment and before its reduction with hydrogen.

The mass of the catalytically active composition of the catalyst after its last heat treatment and before its reduction with hydrogen is defined as the sum of the masses of the catalytically active constituents, where in the case of the abovementioned catalysts prepared by peptization, impregnation or precipitation, materials used as catalyst supports are included as part of the catalytically active composition.

The catalytically active composition of the catalysts used in the process of the present invention can further comprise one or more elements (oxidation state 0) or their inorganic or organic compounds selected from groups I A, II A, III A, IV A, V A, VI A, I B, II B, III B, IV B and V B of the Periodic Table.

Examples of such elements or their compounds are:
transition metals such as Mn or $Mn_2O_3$ or $MnO2$; V or vanadium oxides or vanadyl pyrophosphate; Nb or niobium oxides or niobium oxalate; Ta or tantalum oxides; lanthanides such as Ce or $CeO_2$ or Pr or $Pr_2O_3$; alkali metal oxides such as $Na_2O$; alkali metal carbonates; alkaline earth metal oxides such as MgO, CaO, SrO and BaO; alkaline earth metal carbonates such as $MgCO_3$, $CaCO_3$ and $BaCO_3$; boron oxide ($B_2O_3$).

In the process of the present invention, preference is given to using catalysts which have been prepared by impregnation, precipitation or peptization and whose catalytically active composition before reduction with hydrogen comprises from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or silicon dioxide ($SiO_2$) and/or carbon as activated carbon or graphite, from 1 to 70% by weight, preferably from 2 to 65% by weight, particularly preferably from 4 to 60% by weight, very particularly preferably from 20 to 60% by weight, of oxygen-containing compounds of copper, calculated as CuO, from 0 to 70% by weight, preferably from 1 to 70% by weight, particularly preferably from 5 to 66% by weight, of oxygen-containing compounds of nickel, calculated as NiO, and from 0 to 50% by weight, preferably from 0 to 30% by weight, for example from 0.1 to 25% by weight, of oxygen-containing compounds of cobalt, calculated as CoO, oxygen-containing compounds of chromium, calculated as $Cr_2O_3$, oxygen-containing compounds of zinc, calculated as ZnO, oxygen-containing compounds of molybdenum, calculated as $MoO_3$, oxygen-containing compounds of manganese, calculated as $MnO_2$, oxygen-containing compounds of magnesium, calculated as MgO, oxygen-containing compounds of calcium, calculated as CaO, and/or oxygen-containing compounds of barium, calculated as BaO.

The sum of the abovementioned constituents of the catalytically active composition is usually from 70 to 100% by weight, particularly from 80 to 100% by weight, in particular from 90 to 100% by weight, very particularly from 95 to 100% by weight, for example 100% by weight.

Examples of such catalysts are the catalysts disclosed in DE-A-19 53 263 comprising cobalt, nickel and copper and aluminum oxide and/or silicon dioxide and having a metal content of from 5 to 80% by weight, based on the total catalyst, where the catalysts comprise, calculated on the basis of the metal content, from 70 to 95% by weight of a mixture of cobalt and nickel and from 5 to 30% by weight of copper and the weight ratio of cobalt to nickel is from 4:1 to 1:4, for example the catalysts described in loc. cit. in the examples, which comprise from 2 to 4% by weight of copper oxide, 10% by weight of cobalt oxide and 10% by weight of nickel oxide on aluminum oxide, the catalysts disclosed in EP-A-382 049, whose catalytically active composition before reduction with hydrogen comprises from 20 to 85% by weight of $ZrO_2$, from 1 to 30% by weight of CuO and from 1 to 40% by weight of each of CuO and NiO, for example the catalysts described in loc. cit. on page 6 which have the composition 76% by weight of Zr, calculated as $ZrO_2$, 4% by weight of Cu, calculated as CuO, 10% by weight of Co, calculated as CoO, and 10% by weight of Ni, calculated as NiO, the catalysts disclosed in EP-A-696 572, whose catalytically active composition before reduction with hydrogen comprises from 20 to 85% by weight of $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$ respectively, for example the catalyst disclosed in loc. cit., page 8, which has the composition 31.5% by weight of $ZrO_2$, 50% by weight of NiO, 17% by weight of CuO and 1.5% by weight of $MoO_3$, the catalysts disclosed in the German application No. 19826396.1 of Jun. 12, 1998, whose catalytically active composition before reduction with hydrogen comprises from 22 to 40% by weight of $ZrO_2$, from 1 to 30% by weight of oxygen-containing compounds of copper, calculated as CuO, from 15 to 50% by weight of oxygen-containing compounds of nickel, calculated as NiO, with the molar Ni:Cu ratio being greater than 1, from 15 to 50% by weight of oxygen-containing compounds of cobalt, calculated as CoO, from 0 to 10% by weight of oxygen-containing compounds of aluminum and/or manganese, calculated as $Al_2O_3$ and $MnO_2$ respectively, and no oxygen-containing compounds of molybdenum, for example the catalyst (A) disclosed in loc. cit., page 17, which has the composition 33% by weight of Zr, calculated as $ZrO_2$, 28% by weight of Ni, calculated as NiO, 11% by weight of Cu, calculated as CuO, and 28% by weight of Co, calculated as CoO, the catalysts disclosed in the German application No. 19742911.4 of Sep. 29, 1997, whose catalytically active composition before reduction with hydrogen comprises from 20 to 85% by weight of $ZrO_2$, from 1 to 30% by weight of oxygen-containing compounds of copper, calculated as CuO, from 14 to 70% by weight of oxygen-containing compounds of nickel, calculated as NiO, with the Ni:Cu ratio being greater than 1, from 0 to 10% by weight of oxygen-containing compounds of aluminum and/or manganese, calculated as $Al_2O_3$ and $MnO_2$ respectively, and no oxygen-containing compounds of cobalt or molybdenum, for example the catalyst (A) disclosed in loc. cit., page 14 to 15, which has the composition 32% by weight of Zr, calculated as $ZrO_2$, 51% by weight of Ni, calculated as NiO, and 17% by weight of Cu, calculated as CuO, the catalysts which are disclosed in EP-A-284 919 and have the formula $M_xMg_y(SiO_2) \cdot nH_2O$, where M is a divalent, reducible metal atom selected from the group consisting of Cu, Fe, Co and Ni, x and y are numbers which together can reach the value 1.5 and n is, expressed in % by weight after drying, from 0 to 80, for example the catalyst described in loc. cit. in the example which comprises 35% of CuO, 9% of MgO and 38% of $SiO_2$ and the catalyst described in EP-A-863 140 on page 3 which comprises from 45 to 47% by weight of CuO, magnesium silicate comprising from about 15 to 17% by weight of MgO and from 35 to 36% by weight of $SiO_2$, about 0.9% by weight of $Cr_2O_3$, about 1% by weight of BaO and about 0.6% by weight of ZnO, the catalysts which are disclosed in-DE-A-24 45 303 and are obtainable by heat-treating a basic copper- and aluminum-containing carbonate of the composition $Cu_mAl_6(CO_3)_{0.5m}O_3(OH)_{m+12}$, where m is any, even nonintegral, number from 2 to 6, at from 350 to 700° C., for example the copper-containing precipitated catalyst disclosed in loc. cit., Example 1, which is prepared by treating a solution of copper nitrate and aluminum nitrate with sodium bicarbonate and subsequently washing, drying and heat-treating the precipitate, the supported catalysts disclosed in WO 95/32171 and EP-A-816 350 comprising from 5 to 50% by weight, preferably from 15 to 40% by weight, of copper, calculated as CuO, from 50 to 95% by weight, preferably from 60 to 85% by weight, of silicon, calculated as $SiO_2$, from 0 to 20% by weight of magnesium, calculated as MgO, from 0 to 5% by weight of barium, calculated as BaO, from 0 to 5% by weight of zinc, calculated as ZnO, and from 0 to 5% by weight of chromium, calculated as $Cr_2O_3$, in each case based on the total weight of the calcined catalyst, for example the catalyst disclosed in EP-A-816 350, page 5, which comprises 30% by weight of CuO and 70% by weight of $SiO_2$, the catalysts disclosed in EP-A-514 692, whose catalytically active composition before reduction with hydrogen comprises from 5 to 100% by weight of an oxide of copper and nickel in an atom ratio of from 1:1 to 10:1 and zirconium oxide and/or aluminum oxide, in particular the catalysts disclosed in loc. cit. on page 3, lines 20 to 30, whose catalytically active composition before reduction with hydrogen comprises from 20 to 80% by weight, particularly from 40 to 70% by weight, of $Al_2O_3$ and/or $ZrO_2$, from 1 to 30% by weight of CuO, from 1 to 30% by weight of NiO and possibly from 1 to 30% by weight of CoO, for example the catalyst described in loc. cit., Example 1, which comprises (after activation) 55% by weight of $Al_2O_3$, 36% by weight of Cu and 7% by weight of Ni, the catalysts disclosed in EP-A-691 157 comprising (before reduction with $H_2$) from 85 to 100% by weight, in particular from 95 to 100% by weight, of copper oxide and zirconium dioxide and from 0 to 15% by weight, in particular from 0 to 5% by weight, of metal oxides of transition groups Ib to VIIb and VIII of the Periodic Table, for example the catalyst described in loc. cit., pages 5 to 6, which has the composition 52.6% by weight of CuO and 47.4% by weight of $ZrO_2$, the catalysts disclosed in EP-A-839 575 comprising, based on the total weight of the catalyst, more than 6 and up to 50% by weight of cobalt, nickel or a mixture thereof, from 0.001 to 25% by weight of ruthenium, from 0 to 10% by weight of copper and from 0 to 5% by weight of promoters on a porous metal oxide support such as aluminum oxide, aluminosilicate, titanium dioxide, zirconium dioxide, magnesium oxide or a mixture thereof, which catalysts can be prepared by (a) impregnating the support with the metals, promoters or compounds thereof, (b) drying and calcining the impregnated support and (c) reducing the calcined support in a stream of hydrogen, the catalysts disclosed in EP-A-839 574 comprising, based on the total weight of the catalyst, from 0.1 to 6% by weight of cobalt, nickel or a mixture thereof, from 0.001 to 25% by weight of ruthenium, from 0 to 10% by weight of copper and from 0 to 5% by weight of promoters on a porous metal oxide support such as aluminum oxide, aluminosilicate, titanium dioxide, zirconium dioxide, magnesium oxide or a mixture thereof, which catalysts can be prepared by (a) impregnating the support with the metals, promoters or compounds thereof, (b) drying and calcining the impregnated support and (c) reducing the calcined support in a stream of hydrogen, and the catalysts disclosed in the German Application No. 19859776.2 of Dec. 23, 1998 comprising copper and oxygen-containing compounds of titanium, where the catalyst is used in the form of shaped bodies which have been produced with addition of metallic copper powder, for example catalysts whose catalytically active composition before reduction with hydrogen comprises from 20 to 83% by weight of oxygen-containing compounds of titanium, calculated as $TiO_2$, from 15 to 60% by weight of oxygen-containing compounds of copper, calculated as CuO, and from 2 to 29% by weight of metallic copper which has been added before shaping the catalyst material.

In the process of the present invention, particular preference is given to catalysts which have been prepared by impregnation, precipitation or peptization and whose catalytically active composition contains less than 20% by weight, preferably less than 10% by weight, in particular less than 5% by weight and very particularly less than 1% by weight, of cobalt, calculated as CoO. Very particularly preferably, the catalytically active composition contains no catalytically active amounts of cobalt or its compounds.

In the process of the present invention, very particular preference is given to using catalysts which have been prepared by impregnation, precipitation or peptization and whose catalytically active composition before reduction with hydrogen comprises from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or silicon dioxide ($SiO_2$).

In particular, use is made of catalysts whose catalytically active composition before reduction with hydrogen comprises from 35 to 75% by weight of aluminum oxide ($Al_2O_3$), from 20 to 60% by weight of oxygen-containing compounds of copper, calculated as CuO, and from 5 to 45% by weight, preferably from 5 to 20% by weight, of oxygen-containing compounds of nickel, calculated as NiO, where the sum of these components is at least 80% by weight, preferably at least 90% by weight, particularly preferably at least 95% by weight, for example 100% by weight. Such catalysts can be prepared, for example, as described in EP-A-514 692, page 3, lines 24 to 30. For example, loc. cit., Example 1, describes a catalyst comprising (after activation) 55% by weight of $Al_2O_3$, 36% by weight of Cu and 7% by weight of Ni.

The radicals $R^1$, $R^2$ and $R^3$ of the optically active amines of the formula I

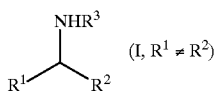

used in the process of the present invention are, independently of one another, alkyl, cycloalkyl, arylalkyl, aryl, heteroaryl and heterocyclic radicals and $R^3$ can also be hydrogen (H), where the radicals may be substituted by substituents which are inert under the reaction conditions and are selected from the group consisting of alkyl, cycloalkyl, alkoxy, aryloxy, amino, alkylamino and dialkylamino and where, in addition, $R^1$ and $R^2$ are different.

$R^1$, $R^2$ and $R^3$ are preferably:
linear or branched alkyl radicals such as $C_1$–$C_{20}$-alkyl, particularly preferably $C_1$–$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl, isododecyl, very particularly preferably $C_1$–$C_8$-alkyl, such as methyl, ethyl, n-propyl, isopropyl, n-butyl, isobutyl, sec-butyl, tert-butyl and 2-ethylhexyl, cycloalkyl radicals, preferably $C_3$–$C_8$-cycloalkyl, such as cyclopropyl, cyclobutyl, cyclopentyl, cyclohexyl, cycloheptyl and cyclooctyl, particularly preferably cyclopentyl, cyclohexyl and cyclooctyl, very particularly preferably cyclopentyl and cyclohexyl, arylalkyl radicals, preferably $C_7$–$C_{20}$-arylalkyl, such as benzyl, 1-phenethyl, 2-phenethyl, 1-naphthylmethyl, 2-naphthylmethyl, phenanthrylmethyls, 4-tert-butylphenyl-methyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, aromatic radicals, preferably $C_6$–$C_{20}$-aryl, such as phenyl, 1-naphthyl, 2-naphthyl, 1-anthryl, 2-anthryl, 9-anthryl, particularly preferably phenyl, 1-naphthyl and 2-naphthyl, particularly preferably phenyl, heteroaromatic radicals, preferably $C_3$–$C_{15}$-heteroaryl, such as 2-pyridyl, 3-pyridyl, 4-pyridyl, quinolyl, pyrazyl, pyrrol-3-yl, thienyl, imidazol-2-yl, 2-furanyl and 3-furanyl, and heterocyclic radicals, preferably $C_3$–$C_{15}$-heterocycloalkyl, such as N-alkylpiperidin-3-yl, N-alkylpiperidin-4-yl, N,N'-dialkylpiperazin-2-yl, tetrahydrofuran-3-yl and N-alkylpyrrolidin-3-yl, where in these cases the radicals R can, independently of one another, bear substituents which are inert under the reaction conditions, e.g. $C_1$–$C_{20}$-alkyl, $C_3$–$C_8$-cycloalkyl, $C_1$–$C_{20}$-alkoxy, $C6$–$C_{20}$-aryloxy, amino, $C_1$–C20-alkylamino and C2–C20-dialkylamino.

The number of these substituents on R can be, depending on the type of radical, from 0 to 5, preferably from 0 to 3, in particular 0, 1 or 2. Possible substituents are, in particular:

$C_1$–$C_{20}$-alkyl, as defined above,

C3–$C_8$-cycloalkyl, as defined above, $C_1$–$C_{20}$-alkoxy, preferably $C_1$–$C_8$-alkoxy, such as methoxy, ethoxy, n-propoxy, isopropoxy, n-butoxy, isobutoxy, sec-butoxy, tert-butoxy, n-pentoxy, isopentoxy, sec-pentoxy, neo-pentoxy, 1,2-dimethylpropoxy, n-hexoxy, isohexoxy, sec-hexoxy, n-heptoxy, isoheptoxy, n-octoxy, isooctoxy, particularly preferably $C_1$–$C_4$-alkoxy, such as methoxy, ethoxy, n-propoxy, isopropoxy, n-butoxy, isobutoxy, sec-butoxy and tert-butoxy, $C6$–$C_{20}$-aryloxy, such as phenoxy, 1-naphthoxy and 2-naphthoxy, preferably phenoxy, amino (—$NH_2$), $C_2$–$C_{20}$-dialkylamino, preferably $C_2$–$C_{12}$-dialkylamino, particularly $C_2$–$C_8$-dialkylamino, for example N,N-dimethylamino, N,N-diethylamino, N,N-di-n-propylamino, N,N-di-isopropylamino, N,N-di-n-butylamino, N-ethyl-N-methylamino, N-methyl-N-propylamino and dicyclohexylamino, and $C_1$–$C_{20}$-alkylamino, preferably $C_1$–$C_{12}$-alkylamino, particularly $C_1$–$C_8$-alkylamino, such as methylamino, ethylamino, n-propylamino, isopropylamino, n-butylamino, isobutylamino, tert-butylamino, cyclopentylamino and cyclohexylamino.

$R^3$ is very particularly preferably hydrogen (H).

Examples of amines I which can be used in the process of the present invention are:

1-methoxy-2-aminopropane (MOIPA), 2-amino-3-methylbutane, 2-amino-3,3-dimethylbutane, 1-phenylethylamine, 1-naphthyl-ethylamine, 2-naphthylethylamine, 1-phenylpropylamine, 2-amino-1-phenylpropane, 2-amino-1-(p-hydroxyphenyl) propane, 2-amino-1-(p-trifluoromethylphenyl)propane, 2-amino-1-cyclohexylpropane, 2-amino-6-methylheptane, 2-aminoheptane, 2-amino-4-methylhexane, 1-(4-methylphenyl)ethylamine, 1-(4-methoxyphenyl)ethylamine, 1-(3-methoxyphenyl) ethylamine, 1-aminotetralin, trans-1-amino-2-benzyloxycyclopentane and trans-1-amino-2-benzyloxycyclohexane.

Particular preference is given to 1-methoxy-2-aminopropane, 2-amino-3-methylbutane and 2-amino-3,3-dimethylbutane.

In a particular variant, the process of the present invention is carried out using an optically active amine I which has been obtained by cleavage of an amide derived from this optically active amine, which amide is formed in the preparation of one enantiomer of I (based on the asymmetric carbon atom shown in I) by (a) enantioselective acylation of the racemic amine I with an ester whose acid component bears a fluorine, nitrogen, phosphorus, oxygen or sulfur atom adjacent to the carbonyl carbon in the presence of a hydrolase and (b) separation of the resulting mixture of optically active amine I and amide.

In a further particular variant, the process of the present invention is carried out using an optically active amine I which has been obtained in the preparation of one enantiomer of I (based on the asymmetric carbon atom shown in I) by (a) enantioselective acylation of the racemic amine I with an ester whose acid component bears a fluorine, nitrogen, phosphorus, oxygen or sulfur atom adjacent to the carbonyl carbon in the presence of a hydrolase, (b) separation of the resulting mixture of optically active amine I and amide and (c) isolation of the other enantiomer of I by cleavage of the amide.

The methods of preparing optically active amines I from the corresponding racemates by (a) enantioselective acylation of the racemic amine I with an ester whose oxygen component bears a fluorine, nitrogen, phosphorus, oxygen or sulfur atom adjacent to the carbonyl carbon in the presence of a hydrolase and (b) separation of the resulting mixture of optically active amine I and amide and (c) isolation of the other enantiomer of I by cleavage of the amide are described in WO 95/08636 and WO 96/23894.

The hydrolase is, for example, a lipase, in particular a microbial lipase. The ester is, for example, a $C_1$–$C_{12}$-alkyl ester of a $C_1$–$C_4$-alkoxy acetic acid, e.g. ethyl methoxyacetate.

The cleavage of the amide derived from the optically active amine I with retention of the configuration of the center of chirality can be carried out by hydrolysis, for example by hydrolysis in the presence of a polyol or an aminoalcohol and an alkali metal hydroxide or alkaline earth metal hydroxide as described in WO 97/10201.

These particular process variants are particularly economical since, after the preparation of the desired enantiomer of the amine I, e.g. as described in WO 95/08636 or WO 96/23894, the remaining, undesired enantiomer of I is racemized by the process of the present application and is returned to the process for preparing the desired enantiomer of I, e.g. as described in WO 95/08636 or WO 96/23894. In this way it is possible to obtain a total of more than 50% of the desired enantiomer from the racemic amine I. (cf. also the discussion on page 1 of the present description, 2nd paragraph).

EXAMPLES

Example 1

Continuous Racemization of (R)-MOIPA in the Gas Phase (R)-1-Methoxyisopropylamine ((R)-MOIPA) together with ammonia and hydrogen were fed via a preheater into a tube reactor operated at 15 bar gauge pressure. The reactor was at 190 to 210° C.; and the circulating gas flow was about 7 standard $m^3/(l_{cat.}*h)$. A small gas output of 300 standard $l/(l_{cat.}*h)$ was taken off.

The reactor had been charged with a precipitated catalyst having the composition 45% by weight of CuO, 10% by weight of NiO and 45% by weight of γ-$Al_2O_3$ support. Before commencement of the reaction, the catalyst was reduced at 240° C. in a stream of hydrogen. The molar ratio of (R)-MOIPA to ammonia was 1:6 and the space velocity over the catalyst was 0.3 kg of (R)-MOIPA and 0.29 kg of ammonia per liter of catalyst (bed volume) and per hour.

The reactor output was depressurized in a separator and worked up by distillation.

GC analysis of the product (ammonia- and water-free) in % by CC area:

(R)–+(S)-MOIPA 92.5 [HPLC: (R)-MOIPA: (S)-MOIPA=50.3:49.7]

| | |
|---|---|
| Methanol | 0.3 |
| Isopropylamine | 0.6 |
| Methoxyisopropanol | 1.1 |
| Octylamine | 2.1 |
| Octanol | 0.2 |
| Others | 3.2 |
| Degree of racemization: | 99% |
| Racemate yield: | 92% |

Example 2

Continuous Racemization of (S)-pinacolylamine ((S)-2-amino-3,3-dimethylbutane) in the Gas Phase Pinacolylamine (purity: 90% of (S)-enantiomer, 10% pinacolone) together with ammonia and hydrogen were fed via a static mixer and preheater into a tube reactor operated at atmospheric pressure (temperature: 160–200° C., single passage). The reactor had been charged with catalyst (for composition, see below), e.g. 3×3 mm pellets. The reactor output was condensed and additional product was collected in a cold trap. The product was analyzed by means of chiral HPLC.

The results are summarized in the following table:

TABLE

| | | | |
|---|---|---|---|
| Preheater temperature, outlet | | 201 | ° C. |
| Reactor temperature, inlet | | 200 | ° C. |
| Reactor temperature, outlet | | 201 | ° C. |
| Feed: | Starting material | 16 | ml/h |
| | $H_2$ | 37 | l/h |
| | $NH_3$ | 16 | l/h |
| Reactor volume | | 110 | ml |

| Catalyst No. | Temperature ° C. | Yield of pinacolylamine % by GC area | Pinacolone % by GC area | ee % | Degree of racemization % |
|---|---|---|---|---|---|
| 1 | 160 | 98.5 | 0.1 | 10.8 | 81 |
| 1 | 180 | 97.7 | 0.5 | 0.25 | 99.5 |
| 1 | 200 | 96.8 | 0.1 | 0.4 | 99.2 |
| 2 | 160 | 98.8 | 0.1 | 0.55 | 98.9 |
| 2 | 180 | 96.4 | 0.6 | 0.73 | 98.5 |
| 2 | 200 | 93.8 | 0.2 | 2.4 | 95.3 |
| 3 | 160 | 98.5 | <0.1 | 1.6 | 96.8 |
| 3 | 180 | 97.6 | 0.2 | 0.14 | 99.7 |
| 3 | 200 | 96.2 | <0.1 | 0.18 | 99.6 |

| Catalyst No. | Composition | | | |
|---|---|---|---|---|
| 1 | 20% Cu | 32% CuO | 48% $TiO_2$ | |
| 2 | 10% NiO | 10% CoO | 4% CuO | 76% $Al_2O_3$ |
| 3 | 53% CuO | 47% $Al_2O_3$ | | |

Comparative Example 1

Experiment on the racemization of (R)-MOIPA using a method analogous to that of DE-A-29 03 589

10 g of (R)-MOIPA (112 mmol), 70 ml of tetrahydrofuran and 1 g of Raney cobalt were placed in a 0.3 1 autoclave. A pressure of 20 bar was set by means of hydrogen. The autoclave was heated to 160° C. and the $H_2$ pressure was increased to 50 bar. After 12 hours under these conditions, the autoclave was cooled to room temperature, the catalyst was filtered off and the tetrahydrofuran was taken off on a rotary evaporator to leave 2.5 g of product.

Determination of the enantiomeric excess (ee) by HPLC analysis: 4.8%

(S)-MOIPA=47.6% by area
(R)-MOIPA=52.4% by area
GC analysis [% by area]:

| | |
|---|---|
| Tetrahydrofuran: | 0.2 |
| Methoxyisopropanol: | 2.2 |
| (R)- + (S)-MOIPA: | 68.3 |
| Octylamine: | 3.7 |
| Octanol: | 10.0 |
| Total of unknown compounds: | 15.6 |
| Degree of racemization: | 90% |
| Racemate yield: | 61% |

Comparative Example 2

Experiment on the racemization of (S)-3,3-dimethyl-2-aminobutane (pinacolylamine) using a method analogous to that of DE-A-29 03 589

10 g of (S)-pinacolylamine (99% ee) were mixed with 60 g of THF and 1 g of Raney cobalt in a 0.3 l stirring autoclave and stirred for 12 hours under a hydrogen atmosphere at a pressure of 50 bar and a temperature of 165° C.

The reactor contents were then cooled to room temperature, the product was separated from the catalyst and the ratio of enantiomers was determined by means of a chiral HPLC column.

Enantiomeric excess: 99%

GC analysis of the product (ammonia- and water-free) in % by GC area:

| | |
|---|---|
| Pinacolone | 0.1 |
| Pinacolylamine | 99.2 |
| Pinacolol | 0.5 |
| Others | 0.2 |
| Degree of racemization: | 0% |
| Racemate yield: | 99.2% |

We claim:

1. A process for the racemization of optically active amines of the formula I

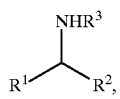

(I)

where $R^1$ and $R^2$ are different and $R^1$, $R^2$, $R^3$ are alkyl, cycoalkyl, arylalkyl, aryl, heteroary and heterocyclic radicals and $R^3$ can be also be hydrogen, where the radicals can bear substituents selected from the group consisting of alkyl, cycloalkyl, alkoxy, aryloxy, amino, alkylamino and dialkylamino, by reaction of the optically active amine at elevated temperature in the presence of hydrogen and a hydrogenation or dehydrogenation catalyst whose catalytically active composition before reduction with hydrogen comprises from 20 to 85% by weight of aluminum oxide ($Al_2O_3$), zirconium dioxide($ZrO_2$), silicon dioxide ($SiO_2$) and/or carbon, from 1 to 70% by weight of oxygen-containing compounds of copper, calculated as CuO, from 0 to 70% by weight of oxygen-containing compounds of nickel, calculated as NiO, and from 0 to 50% by wight of oxygen-containing compounds of cobalt, calculated as CoO, oxygen-containing compounds of chromium, calculated as $Cr_2O3$, oxygen-containing compounds of zinc, calculated as ZnO, oxygen-containing compounds of molybdenum, calculated as $MoO_3$, oxygen-containing compounds of manganese, calculated as $MnO_2$, oxygen-containing compounds of magnesium, calculated as MgO, oxygen-containing compounds of calcium, calculated as CaO, and/or oxygen-containing barium calculated as BaO, wherein the reaction is carried out in the ga phase.

2. A process as claimed in claim 1, wherein the reaction is carried out in the presence of the amine of the formula $R^3NH_2$ in which the radical $R^3$ corresponds to the radical $R^3$ of the optically active amine I.

3. A process as claimed in claim 1, wherein the catalytically active composition of the catalyst comprises the catalytically active constituents copper, silver, gold, iron, cobalt, nickel, rhenium, ruthenium, rhodium, palladium, osmium, iridium, platinum, chromium, molybdenum and/or tungsten in a total amount of from 0.1 to 80% by weight.

4. A process as claimed in claim 1, wherein the catalytically active composition of the catalyst comprises a support material selected from the group consisting of aluminum oxide, zirconium dioxide, titanium dioxide, silicon dioxide and/or carbon in a total amount of from 20 to 99.9% by weight.

5. A process as claimed in claim 1, wherein the reaction is carried out in the presence of a catalyst whose catalytically active composition before reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$).

6. A process as claimed in claim 1, wherein the reaction is carried out in the presence of a catalyst whose catalytically active composition before reduction with hydrogen comprises from 35 to 75% by weight of aluminum oxide ($Al_2O_3$), from 20 to 60% by weight of oxygen-containing compounds of copper, calculated as CuO, and from 5 to 45% by weight of oxygen-containing compounds of nickel, calculated as NiO, where the sum of these components is at least 80% by weight.

7. A process as claimed in claim 1, wherein the reaction is carried out in the presence of a catalyst whose catalytically active composition contains less than 20% by weight of cobalt, calculated as CoO.

8. A process as claimed in claim 1, wherein the reaction is carried out at from 150 to 270° C.

9. A process as claimed in claim 1, wherein the reaction is carried out at a pressure of from 0.1 to 5 MPa.

10. A process as claimed in claim 1, wherein the optically active amine used is 1-methoxy-2-aminopropane, 2-amino-3-methyl-butane or 2-amino-3,3-dimethylbutane.

11. A process as claimed in claim 1, wherein the optically active amine I has been obtained by cleavage of an amide derived from this optically active amine, which amide is formed in the preparation of one enantiomer of I by (a) enantioselective acylation of the racemic amine I with an ester whose acid component bears a fluorine, nitrogen, phosphorus, oxygen or sulfur atom adjacent to the carbonyl carbon in the presence of a hydrolase and (b) separation of the resulting mixture of optically amine I and amide.

12. A process as claimed in claim 1, wherein the optically active amine I has been obtained in the preparation of one enantiomer of I by (a) enantioselective acylation of the racemic amine I with an ester whose acid component bears a fluorine, nitrogen, phosphorus, oxygen or sulfur atom adjacent to the carbonyl carbon in the presence of a hyarolase, (b) separation of the resulting mixture of optically active amine I and amide and (c) isolation of the other enantiomer of I by cleavage of the amide.

* * * * *

UNITED STATES PATENT AND TRADEMARK OFFICE
CERTIFICATE OF CORRECTION

PATENT NO.: 6,160,178

DATED: December 12, 2000

INVENTOR(S): RIECHERS et al.

It is certified that error appears in the above-identified patent and that said Letters Patent is hereby corrected as shown below:

Col. 16, claim 1, line 2, "wight" should be --weight--.

Col. 16, claim 1, line 5, "$Cr_2O3$" should be --$Cr_2O_3$--.

Col. 16, delete claims 3 and 4, which are renumbered original claims 4 and 5, which were canceled in applicants' amendment mailed February 25, 2000.

Signed and Sealed this

Twenty-ninth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.    : 6,160,178
DATED         : December 12, 2000
INVENTOR(S)   : Riechers et al.

It is certified that error appears in the above-identified patent and that said Letters Patent is hereby corrected as shown below:

<u>Column 15,</u>
Line 65, after "($ZrO_2$)," insert -- titanium dioxide ($TiO_2$), --.

Signed and Sealed this

Nineteenth Day of August, 2003

JAMES E. ROGAN
*Director of the United States Patent and Trademark Office*